United States Patent [19]

Stephens et al.

[11] Patent Number: 4,960,763
[45] Date of Patent: Oct. 2, 1990

[54] METHOD OF USING BACTERIAL CELLULOSE AS A DIETARY FIBER COMPONENT

[75] Inventors: R. Scott Stephens, Auburn; John A. Westland, Bothell; Amar N. Neogi, Seattle, all of Wash.

[73] Assignee: Weyerhaeuser Company, Tacoma, Wash.

[21] Appl. No.: 182,670

[22] Filed: Apr. 18, 1988

[51] Int. Cl.$^5$ ............... A61K 31/715; A61K 47/38
[52] U.S. Cl. ........................ 514/57; 514/824; 536/123; 424/439; 426/804
[58] Field of Search ............ 514/57, 824; 424/439; 536/123; 426/804

[56] References Cited

U.S. PATENT DOCUMENTS

| | | | |
|---|---|---|---|
| 4,223,023 | 9/1980 | Furda | 514/55 |
| 4,520,017 | 5/1985 | Tunc | 536/123 |
| 4,535,153 | 8/1985 | Kang et al. | 536/123 |
| 4,567,140 | 1/1986 | Voelskow et al. | 536/123 |
| 4,575,551 | 3/1986 | Fujiyama et al. | 536/123 |
| 4,734,403 | 3/1988 | D'Hinterland et al. | 536/123 |
| 4,798,888 | 1/1989 | Symes et al. | 536/123 |
| 4,801,582 | 1/1989 | Hikino et al. | 536/123 |
| 4,863,565 | 9/1989 | Johnson et al. | 514/781 |

FOREIGN PATENT DOCUMENTS

1570487 10/1975 United Kingdom .

OTHER PUBLICATIONS

Mueller et al., *Jounral of Nutrition*, 113: 2229-2238 (1983).
Ullrich, *Journal of American College Nutrition*, 109: 2085-2097 (1979).
Van Berestayn et al., *Journal of Nutrition*, 109: 2085-2097 (1979).
Jenkins, *Lancet*, 12/15/79, 1287-1290.
Storey et al., *American Journal of Clinical Nutrition*, 31(10): S199-S202 (1978).
Anderson et al, *Federation Proceedings*, 46:877 (1987).
Wilson et al., *Arterial Sclerosis*, 4(2): 147-150 (1984).
Vahouny et al, *American Journal of Clinical Nutrition*, 31(10): S208-S212 (1978).
Lund, *Lipids*, vol. 19, No. 2, 85-89 (1984).
Vahouny et al., *Lipids*, vol. 15, No. 12, 1013-1018 (1980).

*Primary Examiner*—Ronald W. Griffin

[57] ABSTRACT

The invention is a method of binding a portion of the cholesterol present in an aqueous suspension, such as the digestive system of a mammal. It involves the use of a purified bacterial cellulose in a sufficient amount to absorb or bind at least a portion of the cholesterol present in the system. The bacterial cellulose provides a dietary fiber component and is preferably one produced by a bacterium of the genus Acetobacter cultured under agitated aerobic conditions.

30 Claims, No Drawings

METHOD OF USING BACTERIAL CELLULOSE AS A DIETARY FIBER COMPONENT

BACKGROUND OF THE INVENTION

The present invention is a method of binding a portion of the cholesterol or cholesterol ester present in an aqueous system or suspension. This comprises adding a purified bacterial cellulose to the suspension in an amount sufficient to bind at least a portion of the cholesterol present. The method further comprises orally administering bacterial cellulose to mammals in an amount sufficient to absorb at least a portion of the cholesterol or cholesterol ester present in the digestive tract of the mammal.

Arterial plaque buildup has been identified as a major cause of heart attacks and strokes. There is a high correlation between plaque buildup and serum cholesterol content. It is generally accepted that the level of serum cholesterol can be controlled, at least in part, by diet. Physicians generally advocate reduced intake of foods such as egg yolks and organ meats which are naturally high in cholesterol. However, diet is not the only source of cholesterol which enters the mammalian nutritional cycle. A large portion, in fact many authorities believe the major portion, of cholesterol is synthesized in the liver and gall bladder and enters the digestive system through naturally produced bile. Most of the cholesterol, including that from both bile and natural sources, is present in the form of fatty esters. Natural agents cause this to form a suspension in the aqueous system present in the digestive tract.

Effective medication has recently become available for reducing the serum cholesterol level of seriously hypercholesterolemic people. However, this therapy is presently quite expensive and is not without significant side effects. So this treatment is not useful for serum cholesterol level control of the general population.

Various investigators have touted dietary "fiber" as one means of reducing serum cholesterol in humans. The term "fiber" is actually generic to a number of materials which are physically and chemically quite different and which act quite differently in the digestive tract. Mueller et al, *J. Nutrition*, 113: 2229–2238 (1983) identify four major components of fiber. These are cellulose, hemicellulose, lignin and pectins. The first three are generally found in association in plant cell walls and are completely insoluble and resistant to degradation by materials normally found in the gut. They principally serve to provide bulk and hold moisture. They may also serve to somewhat decrease transiton time through the digestive system. While results reported in the literature are equivocal, there seems to be a strong consensus that insoluble fiber does not function to reduce serum cholesterol levels.

"Soluble fiber" is broad category for many pectin-like or gum-like plant derived complex carbohydrates. These are actually water insoluble hydrophilic materials that tend to form bulky gels or slippery products in the digestive system. Some of these appear to have a definite, if minor, effect on blood lipids and lipoproteins. The following articles are cited as being exemplary: Ullrich, *J. Am. Coll. Nutr.*, 6(1): 19–25 (1987); Van Beresteyn et al, *J. Nutrition*, 109: 2085–2097 (1979); Jenkins, *Lancet*, Dec. 15, 1979, pp. 1287–1290; Storey et al, *Amer. J. Clin. Nutr.*, 31(10): S199–S202 (1978).

In one human study Anderson et al, *Federation Proc.*, 46: 877 (1987) reported that a mucilagenous seed coating generally known as psyllium lowered serum cholesterol by an average of 15% and low density lipoproteins by 21% without affecting high density lipoproteins. Cellulose, used as a control material in the tests, had no effect. Other authors as well report the ineffectiveness of cellulose; e.g., Wilson et al, *Arterial Sclerosis*, 4(2): 147–150 (1984); Vahouny et al, *Lipids*, 15(12): 1012–1018 (1980); Storey et al, Ibid.; Vahouny et al, *Am. J. Clin. Nutr.*, 31(10): S208–S212 (1978).

Furda in U.S. Pat. No. 4,223,023 reports that chitosan, used in amounts of 1–10% by weight of food intake, is effective at binding many times its own weight of lipids, preventing their digestion and absorption and promoting their excretion. No clinical data were given, however.

It is evident that there is a pressing need for a dietary supplement that would effectively reduce serum cholesterol levels. Ideally this material would be inexpensive, bland or tasteless, and otherwise chemically neutral or inert. The present inventors have discovered that a previously untried type of cellulose will apparently meet all of these requirements.

SUMMARY OF THE INVENTION

The present invention is a method of binding a portion of the cholesterol present in an aqueous suspension or system. This comprises adding a purified bacterial cellulose to the suspension in an amount sufficient to bind or complex at least a portion of the cholesterol. The invention also comprises a method of reducing the cholesterol present in the digestive tract of mammals by orally administering a sufficient amount of purified bacterial cellulose. The term "cholesterol" is used here to mean either the free or unesterified form or any of the many possible esters.

In view of the previous extensive work that has shown various forms and types of cellulose to be completely ineffective as a cholesterol binder, the present discovery of the usefulness of bacterial cellulose is surprising and completely unexpected.

The preferred bacterial cellulose is one produced by a bacterium of the genus Acetobacter which has been cultured under agitated aerobic conditions. The preferred bacterium is selected from one of the pure strains designated ATCC 53263, 53264, or 53524. These strains are known to be vigorous cellulose producers in agitated culture and are highly resistant to mutation to non-cellulose producing types.

It is an object of the present invention to use a purified bacterial cellulose for binding suspended cholesterol or cholesterol esters.

It is a further object to use a purified bacterial cellulose to bind cholesterol in the digestive tract of mammals.

These and many other objects will become readily apparent upon reading the following detailed description.

DESCRIPTION OF THE PREFERRED EMBODIMENTS

It has been known for many years that cellulose can be synthesized by certain bacteria, particularly those of the genus Acetobacter. However, taxonomists have been unable to agree upon a consistent classification of the cellulose producing species of Acetobacter. For example, the cellulose producing microorganisms listed in the 15th Edition of the Catalog of the American Type Culture Collection under accession numbers 10245, 10821 and 23769 are classified both as *Acetobacter aceti* subsp. *xylinum* and as *Acetobacter pasteurianus*. For the purposes of the present invention any species or variety of bacterium within the genus Acetobacter that will produce cellulose should be regarded as a suitable cellulose producer for the purposes of the present invention.

EXAMPLE 1

Production of Bacterial Cellulose

The bacterial cellulose of the present invention was produced in agitated culture by a strain of *Acetobacter aceti* subsp. *xylinum* grown as a subculture of ATCC Accession No. 53263, deposited Sept. 13, 1985 under the terms of the Budapest Treaty, under conditions similar to the following Example 1.

The following base medium was used for all cultures. This will be referred to henceforth as CSL medium.

| Ingredient | Final conc.(mM) |
| --- | --- |
| $(NH_4)_2SO_4$ | 25 |
| $KH_2PO_4$ | 7.3 |
| $MgSO_4$ | 1.0 |
| $FeSO_4$ | 0.013 |
| $CaCl_2$ | 0.10 |
| $Na_2MoO_4$ | 0.001 |
| $ZnSO_4$ | 0.006 |
| $MnSO_4$ | 0.006 |
| $CuSO_4$ | 0.0002 |
| Vitamin Mix | 10 mL/L |
| Carbon source | As later specified |
| Corn Steep liquor | As later specified |
| Antifoam | 0.01% v/v |

The final pH of the medium was 5.0 ± 0.2.

The vitamin mix was formulated as follows:

| Ingredient | Conc.mg/L |
| --- | --- |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzoic acid | 20 |
| Folic acid | 0.2 |
| Biotin | 0.2 |

Corn steep liquor (CSL) varies in composition depending on the supplier and mode of treatment. A product obtained as Lot E804 from Corn Products Unit, CPC North America, Stockton, California may be considered typical and is described as follows:

| Major Component | % |
| --- | --- |
| Solids | 43.8 |
| Crude protein | 18.4 |
| Fat | 0.5 |
| Crude fiber | 0.1 |
| Ash | 6.9 |
| Calcium | 0.02 |
| Phosphorous | 1.3 |
| Nitrogen-free extract | 17.8 |
| Non-protein nitrogen | 1.4 |
| NaCl | 0.5 |
| Potassium | 1.8 |
| Reducing sugars (as dextrose) | 2.9 |
| Starch | 1.6 |

The pH of the above is about 4.5.

The bacteria were first multiplied as a pre-seed culture using CSL medium with 4% (w/v) glucose as the carbon source and 5% (w/v) CSL. Cultures were grown in 100 mL of the medium in a 750 mL Falcon #3028 tissue culture flask at 30° C. for 48 hours. The entire contents of the culture flask was blended and used to make a 5% (v/v) inoculum of the seed culture. Preseeds were streaked on culture plates to check for homogeneity and possible contamination.

Seed cultures were grown in 400 mL of the above-described medium in 2 L baffled flasks in a reciprocal shaker at 125 rpm at 30° C. for two days. Seed cultures were blended and streaked as before to check for contamination before further use.

Bacterial cellulose for the work to be described later was formed in a continuously stirred 14 L Chemap fermentor using an initial 12 L culture volume inoculated with 5% (v/v) of the seed cultures. An initial glucose concentration of 32 g/L in the medium was supplemented during the 72-hour fermentor run with an additional 143 g/L added intermittently during the run. In similar fashion, the initial 2% (v/v) CSL concentration was augmented by the addition of an amount equivalent to 2% by volume of the initial volume at 32 hours and 59 hours. Cellulose concentration reached about 12.7 g/L during the fermentation. Throughout the fermentation, dissolved oxygen was maintained at about 30% air saturation.

Following fermentation, the cellulose was allowed to settle and the supernatant liquid poured off. The remaining cellulose was washed with deionized water and then extracted with 0.5M NaOH solution at 60° C. for 2 hours. After extraction, the cellulose was again washed with deionized water to remove residual alkali and bacterial cells. More recent work has shown that 0.1M NaOH solution is entirely adequate for the extraction step. The purified cellulose was maintained in wet condition for further use. This material was readily dispersible in water to form a uniform slurry.

The bacterial cellulose produced under stirred or agitated conditions, as described above, has a microstructure quite different from that produced in conventional static cultures. It is a reticulated product formed by a substantially continuous network of branching interconnected cellulose fibers.

The bacterial cellulose prepared as above by the agitated fermentation has filament widths much smaller than softwood pulp fibers or cotton fiber. Typically these filaments will be about 0.05–0.20 microns in width with the indefinite length due to the continuous network structure. A softwood fiber averages about 30 microns in width and 2–5 mm in length while a cotton fiber is about half this width and about 25 mm long.

EXAMPLE 2

Cholesterol Absorption Test and Assay Procedure

The following in vitro procedure was used to test absorption of cholesterol esters by various types of materials which could be generally considered as dietary fiber. 100 to 200 mg (oven dry basis) of the selected fiber material is suspended in 25 mL of a buffer solution which is a 0.1M mixture of mono- and dibasic sodium phosphate at pH 5.4. To this suspension is added from 1 to 5 mL of a cholesterol calibrator solution. Calibration solutions are available as proprietary products from Sigma Chemical Company, St. Louis, Missouri, as Catalog No. C0534. These have either 100, 200, or 400 mg/dL (milligrams per deciliter) of cholesterol in a stable suspension and are supplied in 5 mL quantities. Thus, a 5 mL ampoule at a concentration of 200 mg/dL contains 10 mg of the cholesterol standard. The cholesterol is believed to be largely or completely present in an esterified form held in suspension with a surfactant.

The suspension of fiber with added cholesterol ester is stirred in a beaker for 15 minutes. It then is transferred with water rinsing into centrifuge tubes and centrifuged at 3300 g for 10 minutes, using a type RC5C Sorval centrifuge with a SS34 rotor. The Sorval centrifuge is a product of E. I. duPont de Nemours and Company, Wilmington, Delaware. After centrifuging, the supernatant liquid is decanted and the volume recorded. This supernatant portion is then assayed for remaining cholesterol.

The assay procedure is based on the oxidation of cholesterol and the reaction of the resulting hydrogen peroxide via a peroxidase enzyme with a p-hydroxybenzene sulfonate/4-aminoantipyrine chromogenic system. The necessary reagents are available from Sigma Chemical Company as Test Kit No. 352-20.

To separate labeled tubes are added 0.05 mL water and 0.05 mL of the supernatant solution described above. A standard is made by adding 0.01 mL of the 200 mg/dL cholesterol standard to 0.05 mL water. To each tube is then added 1.0 mL of cholesterol assay solution from the test kit. The tubes are covered with Parafilm M laboratory film, shaken to mix thoroughly, and held at 37° C. for 10 minutes. Parafilm is a trademark of and is available form American Can Company, Greenwich, connecticut. Absorbance at 500 nm is read within 30 minutes using a Spectronic 710 spectrophotometer, available from Bausch and Lomb, Rochester, New York. The concentration of cholesterol in the test solution is proportional to the absorbance based on the standard. The calculation is made as follows:

$$\text{Cholesterol concentration (mg/dL)} = \frac{\text{Absorbance(test)}}{\text{Absorbance(std.)}} \times 200.$$

The value obtained from the above calculation is then multiplied by the volume in deciliters of the supernatant liquid from the centrifuging step.

EXAMPLE 3

Initial Comparison of Bacterial Cellulose with Kraft Cellulose and Psyllium

A sample of bacterial cellulose (BAC), identified as Lot No. A-125, was made as a 5% suspension in water by the general procedure of Example 1 with the exception that it was prepared in a 250 L fermenter. For comparison, a sample of bleached kraft pulp was used. This was made from a furnish consisting of about 80% southern pine and 20% mixed southern hardwoods. It was obtained from Weyerhaeuser Company, New Bern, North Carolina and identified as grade NBF. This particular grade of pulp is generally used as an absorbent fluff material for the manufacture of disposable diapers and similar products.

A second comparison sample was psyllium, Lot No. J60127, marketed as an over-the-counter product by Lafayette Pharmaceuticals, Inc. of Easton, Maryland, as Konsyl psyllium hydrophilic mucilloid. Konsyl is a registered trademark of Lafayette Pharmaceuticals.

Psyllium is widely used as a bulk laxative and is made from the seed coating of one of a number of species of Old World plantains, principally *Plantago ovata* from northwestern India. Less important species include *P. psyllium, P. amplexicaulis, P. decumbens*, and *P. arenaria*. It is considered as a dietary fiber product and has also been shown under some conditions to be effective in reducing serum cholesterol levels.

Initial cholesterol ester concentration added to the suspensions of each of the fiber materials was varied between 0 and 20 mg per 100 mg of product being tested, using the procedure of Example 2. The fiber sample size was 100 mg in each case.

Absorption results obtained are shown in Table I. Very little cholesterol is bound by either the kraft cellulose or the psyllium, whereas the bacterial cellulose effectively bound approximately half of the cholesterol ester initially present. It should be noted that in making the instrumental absorbance readings and calculations, the amount of water retained in the residue in the centrifuge was not taken into account for these tests.

TABLE I

| FIBER ABSORPTION OF CHOLESTEROL-ESTER | | | |
|---|---|---|---|
| Initial Cholesterol (mg) | Bound Cholesterol with 100 mg BAC (mg) | Bound Cholesterol with 100 mg Psyllium (mg) | Bound Cholesterol with 100 mg Kraft Pulp (mg) |
| 0 | 0 | 0 | 0 |
| 1 | 1.00 | 0.00 | 1.00 |
| 5 | 2.01[1] | 0.56 | 1.20 |
| 10 | 4.27 | 1.17 | 1.58 |
| 20 | 6.73 | 1.63 | 1.68 |

[1]Average of six tests

EXAMPLE 4

Comparisons of Bacterial Cellulose with Various Drying Treatments

As was noted, the bacterial cellulose tested in Example 3 was supplied in the form of a never-dried 5% suspension in water. Bacterial cellulose when dried conventionally tends to form a hard, somewhat horny appearing product. In this form it is not well suited for most applications. One way of overcoming this limitation is to freeze dry the product. Another is to dry it subsequent to treatment with a polyol which serves as a "bulking" agent. The polyol replaces in part or totally the water which holds the material in its original physical form. Since the bulking agent is nonvolatile under drying conditions it largely prevents collapse of the microstructure when the water is removed. The bulked product can be either conventionally dried or freeze dried although freeze drying is preferred with bacterial cellulose. Both untreated and bulked samples were freeze dried for the present example to see if the drying treatment had any effect on their performance in absorbing cholesterol.

A first sample consisting of the 5% suspension of bacterial cellulose was formed into a relatively thin layer on the surface of a laboratory scale freeze dryer. This was then frozen at dry ice temperature (approximately −55° C.) and dried under high vacuum. A second sample was first suspended in an approximately 50% sucrose syrup and, after a period of mixing, was freeze dried in similar fashion to the first sample. The bacterial cellulose for both samples was obtained from the same lot number as was the material for Example 3.

The above samples were then treated as described in Examples 2 and 3 with from 0 to 20 mg of cholesterol per 100 mg of bacterial cellulose fiber, using the cholesterol calibrator solutions. Again, sample size was 100 mg in each case. Results of the absorption tests are given in Table II. In this case the water originally present with the fibers was taken into account in the calculations.

TABLE II

CHOLESTEROL-ESTER ABSORPTION USING VARIOUS BACTERIAL CELLULOSE DRYING TREATMENTS

| Initial Cholesterol (mg) | Bound Cholesterol with BAC as is (mg) | Bound Cholesterol with freeze-dried BAC (mg) | Bound Cholesterol with freeze-dried BAC with Sucrose (mg) |
|---|---|---|---|
| 0 | 0 | 0 | 0 |
| 1 | 1.00 | * | 1.00 |
| 5 | 1.71[(1)] | 0.90 | 2.30 |
| 10 | 4.27 | 1.20 | 3.29 |
| 20 | 6.73 | 2.58 | 4.20 |

[(1)]Average of 3 tests

Drying appears to have an adverse effect on cholesterol absorption. However, the use of a bulking agent alleviates some of the loss in absorption efficiency. At the 20 mg cholesterol level, the freeze dried fiber retained about 40% of the binding capacity of the never dried material while the sucrose treated freeze dried fiber retained about 60%. The effect of drying method was less noticeable at lower cholesterol levels. Many polyols besides sucrose would be expected to serve equally well as bulking agents. These include many other sugars including both mono- and disaccharides, sugar alcohols, polyalkylene glycols, etc. Where the product might ultimately be used for mammalian consumption, sugars such as sucrose, glucose, and fructose serve well because of their benign and nontoxic nature.

EXAMPLE 5

Effect of Different Surfactant Levels with Various Fiber Materials

Laboratory tests have shown that the cholesterol calibrator standard materials appear to have a constant amount of surfactant in a given volume of standard regardless of the concentration of cholesterol ester. Stated otherwise, the amount of surfactant does not appear to change regardless of whether the sample contains 100, 200, or 400 mg/dL.

In order to ascertain that the amount of surfactant present in a test sample did not affect absorption results, a series of samples was run at two surfactant levels with other conditions being held constant. The lower surfactant level was achieved by diluting the standard with equal volumes of water. Thus, if it was desired to add 10 mg of cholesterol to the fiber sample being tested, the "high surfactant" sample would be made up using one 5 mL ampoule of 200 mg/dL standard. The "low surfactant" sample would be made using a half ampoule, or 2.5 mL, of a 400 mg/dL standard, and diluting it to 5 mL.

The same fiber materials tested in Example 3 were again tested at the "high" and "low" surfactant levels. In addition, the bacterial cellulose was tested at two levels, this time using 100 mg and 200 mg sample sizes. The other two fibers were tested only using 100 mg samples. In a further difference from Examples 3 and 4, the samples were made up directly in the centrifuge tube, rather than a beaker, to minimize handling losses and transfer washing dilution effects. The capped centrifuge tubes were then shaken 15 minutes on a wrist action shaker prior to centrifuging. The supernatant liquid was then sampled directly from the centrifuge tube for assay. As in Example 4, the water originally present in the fiber samples was taken into effect in subsequent calculations. Total volume is the sum of liquids added plus the amount of water contributed by the fiber.

Results from the "low" surfactant tests are given in Table III and from the "high" surfactant tests in Table IV. These indicate that for all of the fibers tested somewhat higher cholesterol adsorption is seen when the surfactant concentration in the test solution is at the lower level.

TABLE III

CHOLESTEROL-ESTER ABSORPTION LOWER SURFACTANT LEVEL

| Inital Cholesterol (mg) | Bound Cholesterol with 100 mg BAC (mg) | Bound Cholesterol with 200 mg BAC (mg) | Bound Cholesterol with 100 mg Kraft Pulp (mg) | Bound Cholesterol with 100 mg Psyllium (mg) |
|---|---|---|---|---|
| 0 | 0.0 | 0.0 | 0.0 | 0.0 |
| 5 | 1.45 | 2.61 | 0.00 | 0.00 |
| 10 | 2.12 | 3.48 | 0.32 | 0.18 |
| 20 | 2.79 | 4.65 | 1.00 | 1.12 |

TABLE IV

CHOLESTEROL-ESTER ABSORPTION HIGHER SURFACTANT LEVEL

| Initial Cholesterol (mg) | Bound Cholesterol with 100 mg BAC (mg) | Bound Cholesterol with 200 mg BAC (mg) | Bound Cholesterol with 100 mg Kraft Pulp (mg) | Bound Cholesterol with 100 mg Psyllium (mg) |
|---|---|---|---|---|
| 0 | 0.0 | 0.0 | 0.0 | 0.0 |
| 10 | 0.96 | 2.11 | 0.00 | 0.00 |
| 20 | 1.85 | 2.90 | 0.74 | 0.43 |
| 40 | 3.82 | 5.41 | 0.32 | 0.94 |

EXAMPLE 6

Comparison of Different Production Lots of Fibers

In order to check consistency of performance between different production lots of fibers, samples of bacterial cellulose were drawn from Lot No. A-148. This differed from the original Lot No. A-125 in being made in a much larger 6000 L fermenter. A new sample of psyllium designated Lot No. K60107-B, produced by the original manufacturer, was also obtained. These were tested using the procedures of Example 5, again using the "high" and "low" surfactant levels with 100 mg fiber samples.

Results of these tests are given in Table V. These results should be compared with those run under comparable conditions using different lot numbers and given in Tables III and IV. Briefly summarized, the new lot of bacterial cellulose appears to be considerably a more efficient cholesterol absorber than the earlier lot whereas the psyllium is even less effective than the first lot tested. Once again, at least as far as the bacterial cellulose is concerned, absorption was more efficient at the lower surfactant level.

TABLE V

CHOLESTEROL-ESTER ABSORPTION OF BAC LOT #A-148 AND PSYLLIUM LOT #K60107

| Fiber Sample | Initial Cholesterol (mg) | Bound Cholesterol Lower Surfactant Level (mg) | Bound Cholesterol Higher Surfactant Level (mg) |
|---|---|---|---|
| BAC | 5 | 2.28 | * |
| BAC | 10 | 3.48 | 3.48 |
| BAC | 20 | 5.24 | 4.11 |
| BAC | 40 | * | 5.39 |
| Psyllium | 5 | 0.0 | * |
| Psyllium | 10 | 0.0 | 0.0 |
| Psyllium | 20 | 0.0 | 0.0 |
| Psyllium | 40 | * | 0.0 |

EXAMPLE 7

Comparison of Bacterial Cellulose at Various Moisture Levels and Various Lot Numbers with Psyllium and Microcrystalline Cellulose Because of its very high surface area bacterial cellulose is difficult to dewater by conventional means. A 2.5–5% suspension in water is stable and has the appearance of a very soft gel. In Example 4 bacterial cellulose, with and without sucrose bulking, was freeze dried. These materials were compared with a never dried material. Two new techniques were tried to reduce moisture content in the present example. In addition, bacterial cellulose from two different lots produced using yeast extract instead of corn steep liquor as a culture nutrient was tested.

In order to dewater a bacterial cellulose slurry, a sheet of Shark Skin high wet strength filter paper 34 cm in diameter was placed on two sheets of standard TAPPI blotting paper which were about 30 cm on each side. Shark Skin is a trade mark of and is available from Schleicher and Schuell, Keene, New Hampshire. A 3–4 cm thick layer of Lot No. 158 bacterial cellulose slurry at 2.5% solids content was poured onto the filter paper. This was covered with a second filter paper and two additional sheets of blotting paper. The sandwich thus formed was placed between squares of paper machine press felt on the platen of a hydraulic press. The pressure was slowly raised to about 25 kPa and held until no more water dripped from the edges of the felts. At that time the pressure was released and the bacterial cellulose, still between the filter papers, was transferred to a dry blotter pack and again pressed, this time at about 930 kPa. The resultant sheet of pressed bacterial cellulose, now about 2–3 mm thick, was stripped from the filter papers for use. The average moisture content of the product was 47.4%.

A portion of the bacterial cellulose as dewatered above was cut into pieces about 1 cm square, frozen at liquid nitrogen temperature and milled using a RETSCH cryogenic mill to produce a free flowing powdery material at 51.2% solids content. The RETSCH mill is available from Brinkmann, a division of Sybron, Inc., Westbury, New York.

The above bacterial samples were then assayed for cholesterol absorption. For comparison, Lot Nos. A-172 and A-173 bacterial cellulose were also used. As noted, these had been cultured on yeast extract in 6000 L fermenters. For further comparison, Lot No. K60107-B psyllium, as used in Example 6, and Grade PH 101 Avicel were used. Avicel is a microcrystalline cellulose product produced by hydrolysis of cellulose. Avicel is a trademark of and is available from FMC Corporation, Philadelphia, Pennsylvania. This latter product is widely used as a fiber component of control diets for experimental animals and is generally recognized to be ineffective as an in vivo cholesterol absorbent.

The assay procedures used were those of Examples 5 and 6. Results of the tests, all of which used 20 mg of initial cholesterol and 100 mg fiber samples, are given in Table VI.

TABLE VI

CHOLESTEROL ESTER ABSORPTION OF DIFFERENT BAC LOT NUMBERS AND DIFFERENT DRYING PROCEDURES

| FIBER SAMPLE | BOUND CHOLESTEROL, mg |
|---|---|
| BAC A-158(2.5% solids) | 4.78 |
| BAC A-172(1.9% solids) | 4.80 |
| BAC A-173(2.8% solids) | 5.30 |
| BAC A-158(pressed 47.4% solids) | 5.04 |
| BAC A-158(cryo-milled 51.2% solids) | 4.38 |
| Psyllium | 1.03 |
| Avicel | 1.79 |

There does not appear to be differences between the different bacterial cellulose treatments of lot numbers. Cryo-milling does appear to be superior to freeze drying, however. The superiority of bacterial cellulose as a cholesterol absorbent under these test conditions, compared with the control materials, is readily apparent.

All of the above tests were run in vitro. While there is not a perfect correlation between in vitro and in vivo testing, a result obtained in vitro is highly suggestive that a similar result would be expected in vivo. Thus, it can be predicted with some assurance of success that bacterial cellulose will act as a cholesterol binder in the mammalian digestive tract. Bacterial cellulose ingested orally should have definite hypocholesterolemic effects. It can be pointed out that bacterial cellulose and cotton cellulose are chemically nearly identical. They differ only in physical form. On this basis, bacterial cellulose is presumed to be as chemically inert in the gut as are cotton or wood celluloses.

Having herein disclosed the best mode known to the inventors of practicing their invention, it will be apparent to those skilled in the art that many modifications can be made without departing from the spirit of the invention. The scope of the invention is considered to be limited only by the following claims.

We claim:

1. A method of binding a portion of the cholesterol present in an aqueous suspension which comprises adding a sufficient amount of a purified bacterial cellulose to the suspension.

2. The method of claim 1 in which at least a major portion of the cholesterol is present in ester form.

3. The method of claim 1 in which the bacterial cellulose is produced by a bacterium of the genus Acetobacter.

4. The method of claim 3 in which the bacterium is cultured under agitated aerobic conditions.

5. The method of claim 4 in which the bacterium is selected from one of pure strains ATCC 53263, 53264, and 53524.

6. The method of claim 1 in which the bacterial cellulose is bulked with a polyol and dried before use.

7. The method of claim 1 in which the bacterial cellulose is freeze dried prior to use.

8. The method of claim 7 in which the bacterial cellulose is bulked with a polyol prior to freeze drying.

9. The method of claim 6 in which the polyol is sucrose.

10. The method of claim 8 in which the polyol is sucrose.

11. The method of claim 1 in which the bacterial cellulose is cryogenically frozen while still wet and said frozen material is then cryogenically milled to produce a powder-like product before use.

12. A method for binding cholesterol present in the digestive tract of mammals which comprises orally administering thereto an amount of bacterial cellulose sufficient to absorb at least a portion of said cholesterol.

13. The method of claim 12 in which at least a major portion of the cholesterol is present in ester form.

14. The method of claim 12 in which the bacterial cellulose is produced by a bacterium of the genus Acetobacter.

15. The method of claim 14 in which the bacterium is cultured under agitated aerobic conditions.

16. The method of claim 15 in which the bacterium is selected from one of pure strains ATCC 53263, 53264, and 53524.

17. The method of claim 12 in which the bacterial cellulose is bulked with a polyol and dried before use.

18. The method of claim 12 in which the bacterial cellulose is freeze dried prior to use.

19. The method of claim 18 in which the bacterial cellulose is bulked with a polyol prior to freeze drying.

20. The method of claim 17 in which the polyol is sucrose.

21. The method of claim 19 in which the polyol is sucrose.

22. The method of claim 12 in which the bacterial cellulose is cryogenically frozen while still wet and said frozen material is then cryogenically milled to produce a powder-like product before use.

23. A method of providing a source of dietary fiber in a mammalian diet which comprises orally administering an effective amount of bacterial cellulose as a component in the diet of said mammal.

24. The method of claim 23 in which the bacterial cellulose is produced by a bacterium of the genus Acetobacter.

25. The method of claim 24 in which the bacterium is cultured under agitated aerobic conditions.

26. The method of claim 24 in which the bacterium is selected from one of the pure strains ATCC 53263, 53264, and 53524.

27. A dietary supplement having an effective amount of bacterial cellulose as at least one component thereof, said bacterial cellulose providing a source of dietary fiber.

28. The dietary supplement of claim 27 in which the bacterial cellulose is produced by a bacterium of the genus Acetobacter.

29. The dietary supplement of claim 28 in which the bacterium is cultured under agitated aerobic conditions.

30. The dietary supplement of claim 28 in which the bacterium is selected from one of the pure strains ATCC 53263, 53264, and 53524.

* * * * *